US011747635B2

(12) United States Patent
Danziger et al.

(10) Patent No.: US 11,747,635 B2
(45) Date of Patent: Sep. 5, 2023

(54) EYE TRACKER BASED ON RETINAL IMAGING VIA LIGHT-GUIDE OPTICAL ELEMENT

(71) Applicant: LUMUS LTD, Ness Ziona (IL)

(72) Inventors: Yochay Danziger, Kfar Vradim (IL); Eitan Ronen, Rechovot (IL)

(73) Assignee: LUMUS LTD., Ness Ziona (IL)

( * ) Notice: Subject to any disclaimer, the term of this patent is extended or adjusted under 35 U.S.C. 154(b) by 0 days.

(21) Appl. No.: 17/729,241

(22) Filed: Apr. 26, 2022

(65) Prior Publication Data

US 2022/0252890 A1 Aug. 11, 2022

Related U.S. Application Data

(63) Continuation of application No. 16/846,633, filed on Apr. 13, 2020, now abandoned, which is a (Continued)

(51) Int. Cl.
*G02B 27/01* (2006.01)
*A61B 3/113* (2006.01)
(Continued)

(52) U.S. Cl.
CPC .......... *G02B 27/0179* (2013.01); *A61B 3/113* (2013.01); *A61B 3/12* (2013.01);
(Continued)

(58) Field of Classification Search
CPC ............................................. G02B 2027/0178
(Continued)

(56) References Cited

U.S. PATENT DOCUMENTS 4,720,189 A * 1/1988 Heynen .................. A61B 3/113
351/210
6,580,529 B1 * 6/2003 Amitai ............... G02B 27/0944
359/13
(Continued)

FOREIGN PATENT DOCUMENTS

| JP | 2017108370 | 6/2017 |
| WO | WO 2013/145147 | 8/2015 |
| WO | WO2021152602 | 8/2021 |

OTHER PUBLICATIONS

Charles B. Owen et al; "Dismay-Relative Calibration for Optical See-Through Head-Mounted Displays"; Proceedings of the Third IEEE and ACM International Symposium on Mixed and Augmented Reality, Nov. 2-5, Arlington VA, USA, IEEE, Piscataway, NJ, USA, Nov. 2, 2004 (Nov. 2, 2004), pp. 70-78,XP058382672.

*Primary Examiner* — Zachary W Wilkes
(74) *Attorney, Agent, or Firm* — Mark M. Friedman

(57) ABSTRACT

An apparatus (100) for deriving a gaze direction of a human eye (150) includes a light-guide optical element (LOE) (120) having pair of parallel faces (104a), (104b) deployed in facing relation to the eye (150). A coupling-in configuration, such as a set of partially-reflective surfaces (145), is associated with LOE (120) and configured for coupling-in a proportion of light incident on face (104a) so as to propagate within the LOE. Focusing optics (106) associated with LOE (120) converts sets of parallel light rays propagating within the LOE into converging beams of captured light which are sensed by an optical sensor (125). A processing system (108) processes signals from the optical sensor (125) to derive a current gaze direction of the eye. Despite the aperture-combining effect of the LOE, retinal images can be effectively recovered as the only image information brought to focus on the optical sensor.

8 Claims, 12 Drawing Sheets

Related U.S. Application Data continuation of application No. 16/070,782, filed as application No. PCT/IL2017/051408 on Dec. 31, 2017, now abandoned.

(60) Provisional application No. 62/441,205, filed on Dec. 31, 2016.

(51) Int. Cl.
| | |
|---|---|
| *A61B 3/12* | (2006.01) |
| *G02B 27/00* | (2006.01) |
| *G06V 40/19* | (2022.01) |
| *F21V 8/00* | (2006.01) |

(52) U.S. Cl.
CPC ..... *G02B 27/0093* (2013.01); *G02B 27/0172* (2013.01); *G06V 40/19* (2022.01); *G02B 6/0011* (2013.01); *G02B 2027/014* (2013.01); *G02B 2027/0138* (2013.01); *G02B 2027/0178* (2013.01); *G02B 2027/0187* (2013.01)

(58) Field of Classification Search
USPC ........................................................ 359/630
See application file for complete search history.

(56) References Cited

U.S. PATENT DOCUMENTS

| | | | |
|---|---|---|---|
| 6,927,694 | B1 | 8/2005 | Smith et al. |
| 7,573,640 | B2 * | 8/2009 | Nivon ................ G02B 27/4216 359/630 |
| 7,857,444 | B2 | 12/2010 | Moliton |
| 9,170,425 | B1 | 10/2015 | Harrison et al. |
| 9,348,143 | B2 | 5/2016 | Gao et al. |
| 9,513,479 | B2 | 12/2016 | Akira et al. |
| 96,255,723 | | 4/2017 | Xinye et al. |
| 9,740,006 | B2 | 8/2017 | Gao |
| 9,927,614 | B2 | 3/2018 | Vallius |
| 10,007,115 | B2 | 6/2018 | Greenhalgh |
| 10,126,568 | B2 | 11/2018 | Rousseau et al. |
| 10,139,636 | B2 | 11/2018 | Lebrun |
| 10,198,865 | B2 | 2/2019 | Kezele et al. |
| 10,247,962 | B2 | 4/2019 | Rousseau et al. |
| 10,326,983 | B2 | 6/2019 | Hua |
| 10,345,903 | B2 | 9/2019 | Robbins et al. |
| 10,409,064 | B2 | 9/2019 | Lee |
| 10,416,452 | B2 | 9/2019 | Cheng et al. |
| 10,852,549 | B2 | 12/2020 | Rousseau |
| 10,878,235 | B2 * | 12/2020 | Jarvenpaa .......... G02B 27/4216 359/630 |
| 11,175,518 | B2 | 11/2021 | Zimanyi |
| 11,202,563 | B2 | 12/2021 | Zimmany |
| 11,226,261 | B2 | 1/2022 | Lobachinsky et al. |
| 2007/0091445 | A1 | 4/2007 | Amitai |
| 2007/0165192 | A1 | 7/2007 | Prior |
| 2010/0056274 | A1 * | 3/2010 | Uusitalo .............. G02B 27/017 463/31 |
| 2012/0120498 | A1 | 5/2012 | Harrison |
| 2012/0127062 | A1 | 5/2012 | Bar Zeev et al. |
| 2013/0002122 | A1 | 1/2013 | Bell |
| 2013/0021226 | A1 | 1/2013 | Bell |
| 2013/0094712 | A1 | 4/2013 | Said |
| 2013/0012022 | A1 | 5/2013 | Cajigas et al. |
| 2013/0322810 | A1 * | 12/2013 | Robbins .............. G02B 27/0172 385/11 |
| 2015/0138248 | A1 * | 5/2015 | Schrader ............ G02B 27/0093 345/690 |
| 2015/0160460 | A1 | 6/2015 | Komatsu et al. |
| 2016/0018639 | A1 * | 1/2016 | Spitzer ................. G02B 5/3083 359/13 |
| 2016/0018654 | A1 | 1/2016 | Haddick et al. |
| 2016/0189432 | A1 | 6/2016 | Bar Zeev |
| 2016/0198949 | A1 | 7/2016 | Spitzer |
| 2016/0209657 | A1 * | 7/2016 | Popovich ............. G02B 27/017 |
| 2016/0314564 | A1 | 10/2016 | Jones |
| 2017/0003504 | A1 | 1/2017 | Vallius |
| 2017/0017095 | A1 | 1/2017 | Fricker et al. |
| 2017/0242249 | A1 | 4/2017 | Wall |
| 2017/0122725 | A1 | 5/2017 | Yeoh |
| 2017/0277259 | A1 * | 9/2017 | Mullins ................ G02B 27/017 |
| 2018/0335629 | A1 | 11/2018 | Cheong et al. |
| 2019/0018247 | A1 | 1/2019 | Gao et al. |
| 2019/0064519 | A1 | 2/2019 | Ben-Asher et al. |
| 2019/0086674 | A1 | 3/2019 | Sinay et al. |
| 2019/0008667 | A1 | 5/2019 | Sinay et al. |
| 2019/0187482 | A1 | 6/2019 | Lanman |
| 2019/0322382 | A1 | 10/2019 | Mackin |
| 2020/0159030 | A1 | 5/2020 | Ayres |
| 2021/0033774 | A1 | 2/2021 | Tanaka |
| 2022/0004014 | A1 | 1/2022 | Ronen et al. |
| 2022/0107499 | A1 | 4/2022 | Amitai |

* cited by examiner

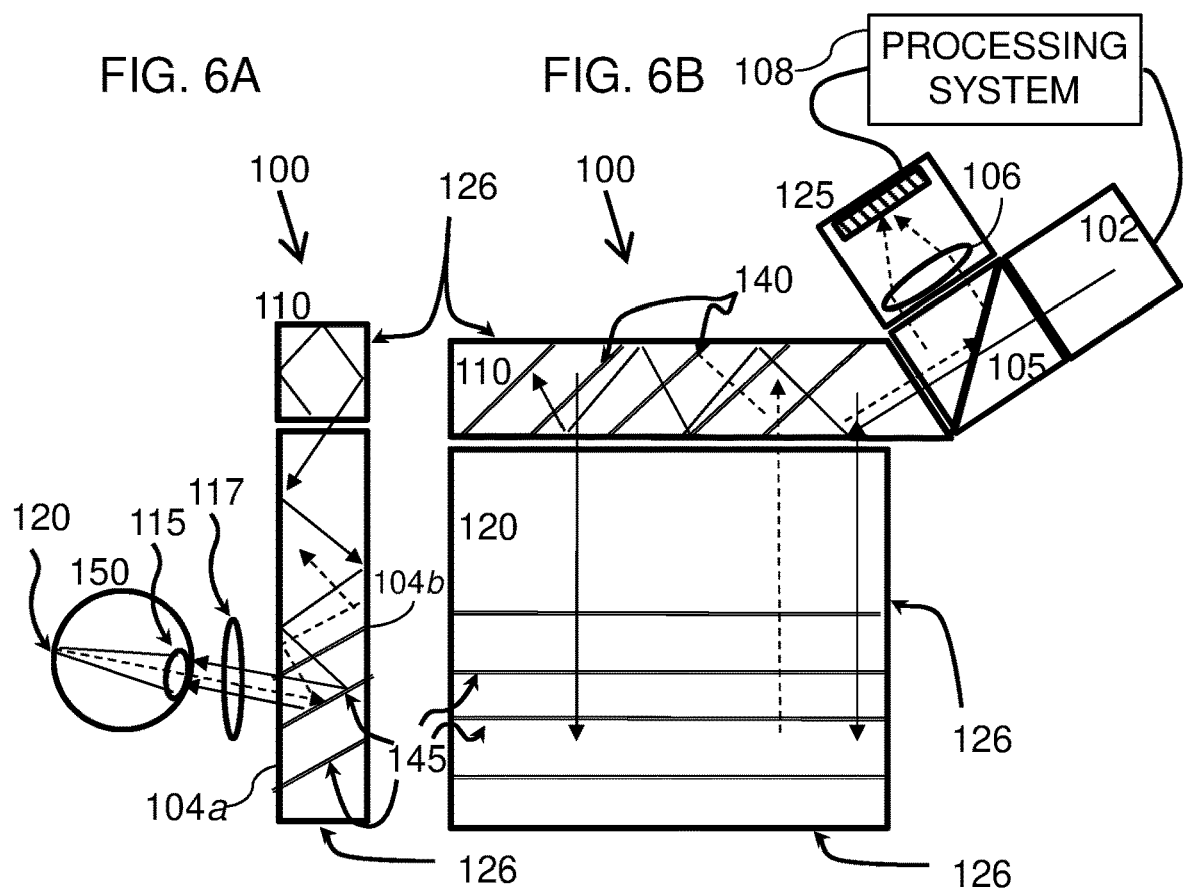
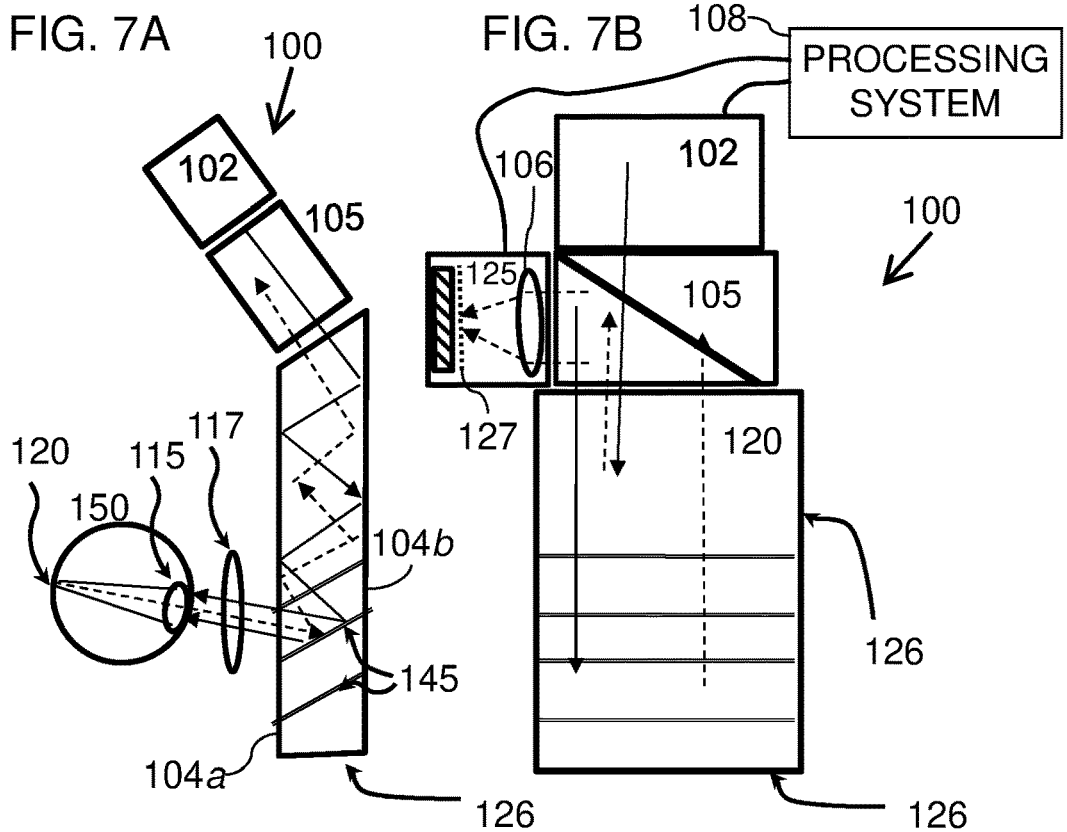

Wavelength responsiveness of short (S), medium (M) and long (L) wavelength cones compared to that of rods (R). [1]

EYE TRACKER BASED ON RETINAL IMAGING VIA LIGHT-GUIDE OPTICAL ELEMENT

FIELD AND BACKGROUND OF THE INVENTION

The present invention relates to eye tracking and, in particular, it concerns an eye tracker and corresponding method for tracking the gaze direction of a human eye based on retinal imaging via a light-guide optical element, particularly suitable for integration as part of a near-eye display.

Optical arrangements for near eye display or head up display require large aperture to cover the area where the observer's eye is located (the eye motion box). In order to implement a compact device, the image is generated by a small optical image generator (projector) having a small aperture that is multiplied to generate a large aperture.

An approach to aperture multiplication in one dimension has been developed based on a parallel-faced slab of transparent material within which the image propagates by internal reflection. Part of the image wavefront is coupled out of the slab, either by use of obliquely angled partial reflectors or by use of a diffractive optical element on one surface of the slab. Such a slab is referred to herein as a "light-guide optical element", "light transmitting substrate" or "waveguide". The principles of such aperture multiplication are illustrated schematically in FIGS. 1-4.

FIG. 1 shows a light-guide optical element 20 having a pair of parallel faces 26, 26A for guiding light by internal reflection. A projected image 18, as represented here schematically by a beam of illumination 18 including sample rays 18A, 18B and 18C which span the beam, is coupled into the light-guide optical element, as illustrated here schematically by a first reflecting surface 16, so as to generate reflected rays 28 which are trapped by internal reflection within the substrate, generating also rays 30. The image propagates along the substrate by repeated internal reflection, impinging on a sequence of partially reflecting surfaces 22 at an oblique angle to the parallel faces 26, 26A, where part of the image intensity is reflected so as to be coupled out of the substrate as rays 48A, 48B. In order to minimize unwanted reflections which might give rise to ghost images, the partially reflecting surfaces 22 are preferably coated so as to have low reflectance for a first range of incident angles, while having the desired partial reflectivity for a second range of incident angles, for example, as illustrated in FIGS. 2A and 2B, where a ray 32 with a small inclination to the normal to a partially reflective surface 34 is split in order to generate a reflected ray for coupling out (FIG. 2A), while a high inclination (to the normal) ray 36 (FIG. 2B) is transmitted with negligible reflection.

FIG. 3 illustrates a corresponding configuration implemented using a diffractive optical element 23 for coupling out of the image, and in the example shown here, another diffractive optical element 17 for coupling in of image 18. The diffractive optical elements may be deployed on either the upper or lower surface of the substrate, as is known in the art.

In both cases, projected image 18 is a collimated image, i.e., where each pixel is represented by a beam of parallel rays at a corresponding angle, equivalent to light from a scene far from the observer. The image is represented here simplistically by rays corresponding to a single point in the image, typically a centroid of the image, but in fact includes a range of angles to each side of this central beam, which are coupled in to the substrate with a corresponding range of angles, and similarly coupled out at corresponding angles, thereby creating a field of view corresponding to parts of the image arriving in different directions to the eye 24 of the observer.

The aperture multiplication of FIGS. 1 and 3 occurs along one dimension, corresponding to the right-to-left direction of the drawings. In some cases, a similar approach is adopted in two dimensions, such as is illustrated in FIG. 4. In this case, a first waveguide 20a has a coupling-in reflector 16a and partially-reflective coupling-out surfaces 22a which provide the optical input to a second waveguide 20b with a coupling-in reflector 16b and partially-reflective coupling-out surfaces 22b. In this manner, an image represented by input ray 90 is multiplied successively in two dimensions to provide an output aperture expanded in two dimensions. Although illustrated here using partially-reflecting surfaces for the coupling-out, one or both of the expansions may be performed using diffractive optical elements.

It will be noted that the relatively large output aperture achieved by aperture multiplication results in each input image ray being split into a plurality of spaced apart output rays. In FIGS. 1 and 3, this is represented by multiple out-coupled rays 48A derived from splitting input ray 18A, and multiple out-coupled rays 48B derived by splitting input ray 18B. The same is true for the two dimensional expansion of FIG. 4.

SUMMARY OF THE INVENTION

One aspect of the present invention provides an eye tracker and corresponding method for tracking the gaze direction of a human eye based on retinal imaging via a light-guide optical element, particularly suitable for integration as part of a near-eye display.

According to the teachings of an embodiment of the present invention there is provided, an apparatus for deriving a gaze direction of a human eye, the apparatus comprising: (a) a light-guide optical element (LOE) formed from transparent material and having pair of parallel faces for guiding light by internal reflection, one of the parallel faces being deployed in facing relation to the eye; (b) a coupling-in configuration associated with the LOE and configured for coupling-in a proportion of light incident on one of the parallel faces within a coupling-in region so as to propagate within the LOE; (c) focusing optics associated with the LOE and configured for converting sets of parallel light rays propagating within the LOE into converging beams of captured light; (d) an optical sensor deployed for sensing the captured light; and (e) a processing system including at least one processor, the processing system being electrically associated with the optical sensor and configured so as to process signals from the optical sensor to derive a current gaze direction of the eye, wherein the coupling-in configuration is configured to generate rays propagating within the LOE, each ray having a direction indicative of a direction of incidence of a corresponding incident light ray, and wherein a plurality of spaced-apart parallel incident rays are combined into a single ray propagating within the LOE.

According to a further feature of an embodiment of the present invention, the coupling-in configuration comprises a plurality of partially-reflective surfaces deployed within the LOE obliquely to the parallel faces.

According to a further feature of an embodiment of the present invention, the coupling-in configuration comprises a diffractive optical element associated with one of the parallel faces.

According to a further feature of an embodiment of the present invention, the optical sensor comprises a four-quadrant sensor.

According to a further feature of an embodiment of the present invention, the optical sensor comprises an array of pixel sensing elements, and wherein the processing system processes outputs from no more than about 104 pixel sensing elements.

According to a further feature of an embodiment of the present invention, there is also provided an illumination arrangement deployed to illuminate the eye from the direction of the coupling-in region.

According to a further feature of an embodiment of the present invention, the illumination arrangement is configured to introduce illumination into the LOE so that the illumination propagates within the LOE by reflection at the pair of parallel surfaces and is coupled out towards the eye by the coupling-in configuration.

According to a further feature of an embodiment of the present invention, there is also provided an illumination light-guide element formed from transparent material and having pair of parallel faces for guiding light by internal reflection, the illumination light-guide element being deployed in overlapping relation to the LOE, wherein the illumination arrangement is configured to introduce illumination into the illumination light-guide element so that the illumination propagates within the illumination light-guide element by reflection at the pair of parallel surfaces and is coupled out towards the eye by a coupling-out configuration associated with the illumination light-guide element.

According to a further feature of an embodiment of the present invention, the illumination arrangement is associated with the processing system, the processing system actuating the illumination arrangement to generate illumination pulses with a pulse duration, and wherein the processing system processes signals derived from the optical sensor corresponding to captured light incident during the pulse duration.

According to a further feature of an embodiment of the present invention, there is also provided a passband spectral filter deployed to obstruct light of wavelengths outside a given range of wavelengths from reaching the optical sensor, and wherein the illumination arrangement generates illumination primarily within the given range of wavelengths.

According to a further feature of an embodiment of the present invention, the given range of wavelengths is in a non-visible region of the electromagnetic radiation spectrum.

According to a further feature of an embodiment of the present invention, the illumination arrangement comprises a plurality of separately controlled illumination pixels, and wherein the processing system selectively actuates the illumination pixels so as to illuminate selectively along directions corresponding to a selected region of the retina of the eye.

According to a further feature of an embodiment of the present invention, during ongoing tracking of the eye gaze direction, the selected region of the retina is a region including the optic disc of the eye.

According to a further feature of an embodiment of the present invention, the processing system is configured to process signals from the optical sensor to derive a center of an intensity distribution corresponding to reflection from the retina of the eye, and thereby to determine the current gaze direction of the eye.

According to a further feature of an embodiment of the present invention, the processing system is configured to process signals from the optical sensor to detect a location of at least one prominent feature of the retina of the eye, and thereby to determine the current gaze direction of the eye.

According to a further feature of an embodiment of the present invention, the processing system is configured to process signals from the optical sensor to track a pattern of blood vessels in the retina of the eye, and thereby to determine the current gaze direction of the eye.

According to a further feature of an embodiment of the present invention, there is also provided an image projector coupled to the LOE so as to introduce a collimated image into the LOE such that the collimated image propagates via internal reflection within the LOE and is coupled out of the LOE towards the eye by the coupling-in configuration.

According to a further feature of an embodiment of the present invention, the image projector is associated with the processing system, and wherein the processing system actuates the image projector to generate illumination pulses with a pulse duration, the processing system processing signals derived from the optical sensor corresponding to captured light incident during the pulse duration.

According to a further feature of an embodiment of the present invention, the processing system generates the pulses so as to correspond to a selected subsection of a projected image, and such that the pulses contribute to perception of the projected image.

According to a further feature of an embodiment of the present invention, there is also provided a support configuration for supporting the apparatus relative to the head of a human user such that the LOE is deployed in facing relation to a first eye of the user, the apparatus further comprising: (a) a second-eye light-guide optical element (LOE) formed from transparent material and having pair of parallel faces for guiding light by internal reflection, one of the parallel faces being deployed in facing relation to a second eye of the user; (b) a coupling-in configuration associated with the second-eye LOE and configured for coupling-in a proportion of light incident on one of the parallel faces within a coupling-in region so as to propagate within the LOE; (c) focusing optics associated with the second-eye LOE and configured for converting sets of parallel light rays propagating within the LOE into converging beams of captured light; and (d) a second-eye optical sensor deployed for sensing the captured light, wherein the processing system is further associated electrically associated with the second-eye optical sensor and configured so as to process signals from both of the optical sensors to derive a current gaze direction of the eyes of the user.

There is also provided according to the teachings of an embodiment of the present invention, a method comprising the steps of: (a) providing the apparatus according to any of the above variants; and (b) processing signals from the optical sensor to derive a current gaze direction of the eye.

BRIEF DESCRIPTION OF THE DRAWINGS

Exemplary embodiments of the invention are herein described, by way of example only, with reference to the accompanying drawings, wherein:

FIGS. 6A and 6B are schematic side and front views, respectively, of the optical architecture of the apparatus of FIG. 5 according to a first preferred implementation;

FIGS. 7A and 7B are schematic side and front views, respectively, of the optical architecture of the apparatus of FIG. 5 according to a second preferred implementation;

DESCRIPTION OF THE PREFERRED EMBODIMENTS

Figure 1:
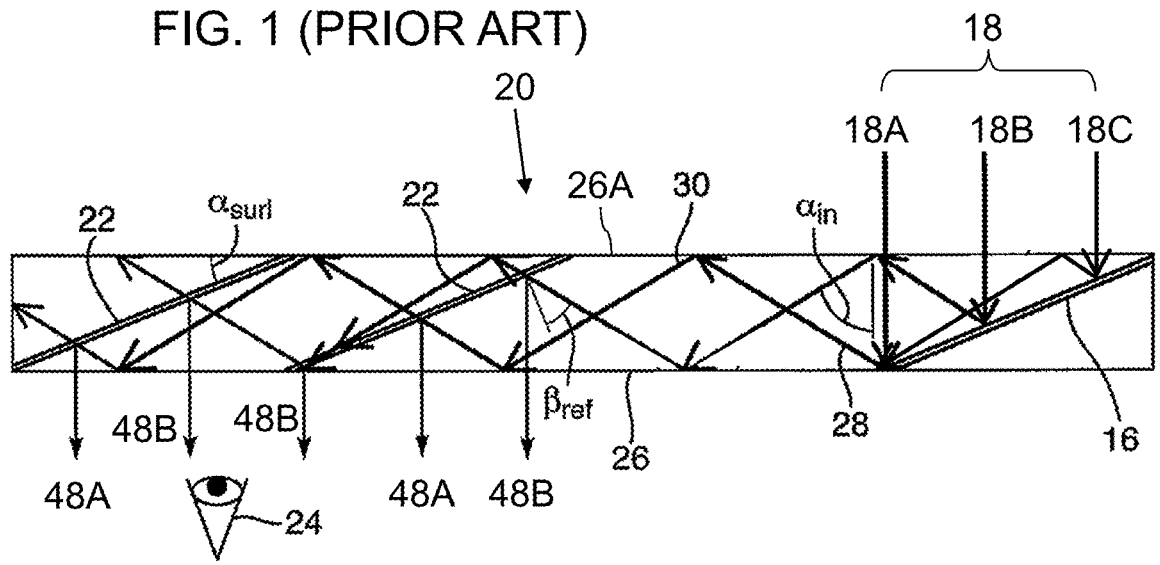
FIG. 1 is a schematic side view, described above, of a prior art light-guide optical element employing partially-reflective surface, for use in a near-eye display.
Figure 2A:
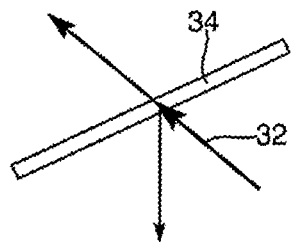
FIGS. 2A and 2B are schematic representations of angularly-selective reflective properties of partially-reflective surfaces used in the prior art display of FIG. 1.
Figure 2B:
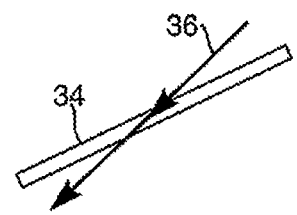

An embodiment of the present invention provides an apparatus and corresponding method for tracking the gaze direction of a human eye based on retinal imaging via a light-guide optical element, particularly suitable for integration as part of a near-eye display.

The principles and operation of an eye tracking apparatus according to the present invention may be better understood with reference to the drawings and the accompanying description.

Referring now to the drawings, FIGS. 5-23 illustrate various aspects of the structure and operation of an apparatus, generally designated 100, constructed and operative according to various embodiments of the present invention, for deriving a gaze direction of a human eye 150.

By way of introduction, in many applications, particularly in the context of head-up or near-eye displays, it is useful to provide an eye tracking arrangement for determining the gaze direction of the user. One common approach for performing eye tracking is to sample an image of the eye, typically for the purpose of determining the pupil position within the image, and thereby deriving the orientation of the eye.

Figure 3:
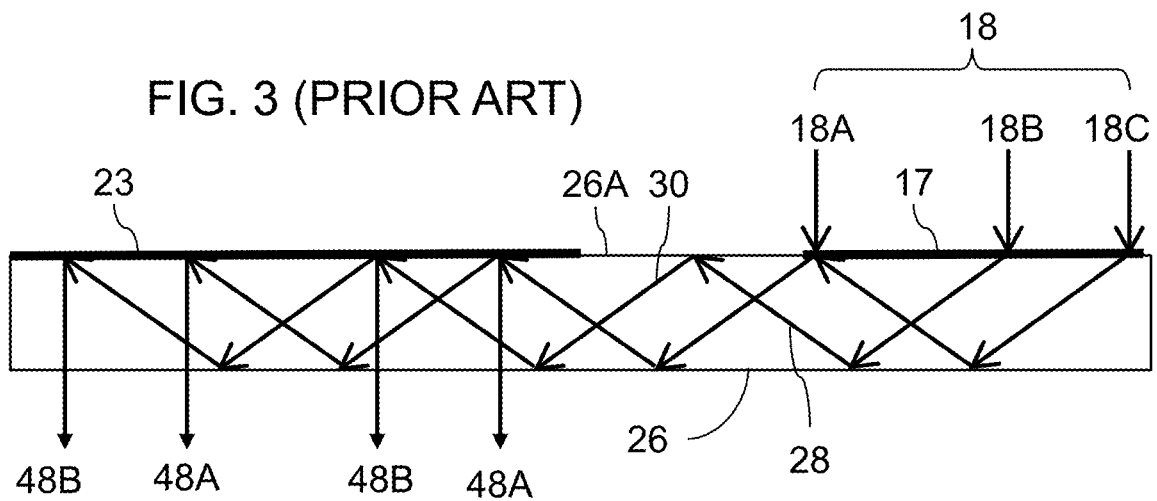
FIG. 3 is a schematic side view, described above, of a prior art light-guide optical element employing diffractive optical elements, for use in a near-eye display.
Figure 4:
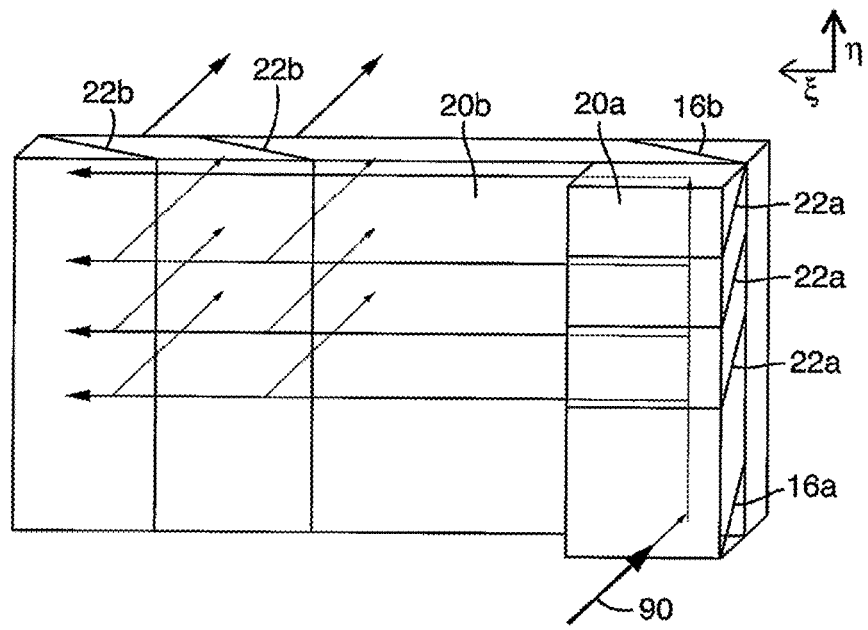
FIG. 4 is a schematic isometric view, described above, of a prior art optical aperture expansion arrangement based upon a combination of two light-guide optical elements similar to that of FIG. 1.

It would be particularly advantageous to employ a light-guide optical element operating on principles similar to those of FIG. 1 or 3 to sample images for eye tracking. However, the one-to-many relationship from the input image to the output image described above with references to FIGS. 1 and 3 results in a converse many-to-one relationship in sampling light in the reverse direction. Specifically, use the aperture multiplying arrangements of FIG. 1 or 3 in the reverse direction for sampling an image would perform superposition of a plurality of parallel rays incident on the substrate from different parts of the field of view of the system. Light arriving along a path corresponding to the reverse of the multiple paths labeled 48A would all be combined into an output ray along the reverse path of ray 18A, and similarly multiple incident rays along the reverse path of ray 48B would be combined to the reverse path of ray 18B. Furthermore, if converging optics is used to focus light captured through the light-guide optical element onto an imaging sensor, all captured light which was incident on the substrate along parallel ray paths from the entire field of view would be combined to fall on a single pixel sensor. Since the light from surfaces of the cornea, sclera, eyelids and facial tissue typically scatters light omnidirectionally (Lambertian reflection), all of the surfaces in the field of view will typically contribute some radiation to all pixels of the image. For these reasons, it would generally not be considered feasible to try to resolve an image from light incident on the light-guide optical element.

The present invention provides an apparatus and method which, despite the above challenges, has been found effective for determining an eye gaze direction from light captured by a light-guide optical element, as will now be described. Specifically, certain particularly preferred embodiments of the present invention provide an apparatus 100 for deriving a gaze direction of a human eye 150 which includes a light-guide optical element (LOE) 120 formed from transparent material and having pair of parallel faces 104*a*, 104*b* for guiding light by internal reflection. The LOE 120 is deployed with one of the parallel faces 104*a* in facing relation to the eye 150. A coupling-in configuration, such as a set of partially-reflective surfaces 145, is associated with LOE 120 and configured for coupling-in a proportion of light incident on face 104*a* within a coupling-in region so as to propagate within the LOE. Focusing optics 106 is associated with LOE 120, directly or indirectly, so as to receive the captured light propagating within LOE 120 and to convert sets of parallel light rays propagating within the LOE into converging beams of captured light. Focusing optics 106 is preferably integrated into an optical sensor or "camera" 125 that is deployed for sensing the captured light. A processing system 108, including at least one processor, is electrically associated with optical sensor 125, and is configured so as to process signals from optical sensor 125 to derive a current gaze direction of the eye.

The coupling-in configuration may be any coupling-in arrangement which deflects part of the incident radiation to an angle which propagates through internal reflection within the LOE, and where each ray has a direction indicative of a direction of incidence of the corresponding incident light ray. Suitable coupling-in configurations include a set of partially-reflective surfaces 145 as shown, and a diffractive optical element.

As explained above, it is an inherent feature of the aperture multiplying configurations of the LOE that, in the reverse (sensor) mode of operation, a plurality of spaced-apart parallel incident rays are combined into a single ray propagating within the LOE. Nevertheless, for retinal imaging, this combining of parallel rays does not preclude derivation of an image. Specifically, for an eye focused on a distant scene (or on a collimated projected image equivalent to a distant scene), the ocular lens, together with any corrective spectacle lens if present, generates an image focused on the retina. It follows that any light reflected from the retinal surface is effectively collimated by the ocular lens (and corrective spectacle lens if present) to form a far-field image, where each feature of the retinal image corresponds to beam of parallel rays of light. The retinal image is therefore preserved as the parallel rays are collected by the LOE, directed into the reduced aperture, and focused by focusing optics 106 towards optical sensor 125. Although the sensed image data includes much scattered light from the near-field external surfaces of the eye and surrounding tissue, the near-field illumination is roughly uniformly distributed in angular space, thereby generating a generally flat background noise in the sampled image. Only the modulation and/or features due to the retinal reflected image generates contrast within the image, thereby facilitating determination of the current gaze direction of the observer. These and other features of the present invention will become clearer from the following detailed description.

Referring now specifically to FIGS. 6A and 6B, this shows one non-limiting exemplary implementation of apparatus 100 of the present invention, in which tracking is performed through a near-eye display arrangement employing optical aperture multiplication. The configuration as shown is based on a combination of two light-guide optical elements: a first LOE 110 which expands a projector image aperture in a first dimension (right-to-left as shown in FIG. 6B) and a second LOE 120 which expands the image aperture in a second dimension (top-to-bottom as illustrated here). An image projector 102 projects light (depicted as solid arrows) through a polarization-selective beam splitter (PBS) 105 onto into LOE 110. In one particularly preferred but non-limiting set of implementations as illustrated here, LOE 110 is a "2D waveguide", meaning that it has two mutually-orthogonal pairs of surfaces which serve to guide the image in two dimensions as it propagates along LOE 110. LOE 120 is a "1D waveguide", meaning that it has one pair of parallel major surfaces defining a "slab-type waveguide" which guides the image in one dimension. In an alternative embodiment as illustrated in FIGS. 7A and 7B, apparatus 100 may be implemented using only one waveguide, LOE 120. The latter case as illustrated here employs a tilted projector coupling-in configuration. Further details of such waveguide configurations and coupling-in configurations in the context of a near-eye display (without eye tracking) can be found in various documents, including WO 2015/162611 A1 and PCT patent application no. PCT/IL2017/051028 (which was unpublished as of the filing date of this application and does not constitute prior art), which are hereby incorporated by reference in their entirety as if set out fully herein. The exemplary embodiments illustrated herein will refer primarily to the two-waveguide implementation of FIGS. 6A and 6B, which is the more complex implementation, while the modifications required to implement the simpler structure of a single waveguide implementation will be self-apparent to a person ordinarily skilled in the art.

Coupling of the image out from LOE 110 into LOE 120 is here shown as performed by a series of internal partially reflective surfaces (or "facets") 140 deployed at an oblique inclination to one or both pairs of parallel surfaces of LOE 110. Coupling out from the second LOE 120 towards the eye of the observer is achieved using a second set of internal partially reflective surfaces ("facets") 145 deployed at an oblique angle to the parallel faces of that substrate, as best seen in the side view of FIGS. 6A and 7A. The facets in one or both of the LOE's may be replaced by diffractive optical elements, as is known in the art. The coupled-out light of the projected image is focused by the eye lens 115 (with the assistance of a spectacle lens 117 if a sight correction needed) to generate a focused image on the retina 120.

According to an exemplary implementation of the present invention, the near-eye display system obtains the line of sight of the observer's eye by imaging patterns that exist on the retina of the observer. The observation is performed via waveguides 120 and 110, which are in this case the same waveguides used for projecting an image to the observer's eye. The position of the patterns and their motion indicate the current line-of-sight and motion of the eye. Such patterns are shown in an image of a retina presented in FIG. 13. The blood vessels 152 generate a pattern that can be tracked by appropriate standard or dedicated tracking algorithm implemented by suitable image processing instructions performed by processing system 108. The fovea 155 determines the direction of observation and the optic disc (or "blind spot") 157 is a characteristic trackable point where nerves and blood vessels converge.

Some of the light is reflected (depicted as dashed arrow) from the retina back through the lens 115, effectively collimating it into a parallel beam, and propagates back along the same optical path taken by light from the projector. A significant part of the light is lost (as discussed further below), but for clarity of presentation, only the part that is useful for tracking is shown. Part of the reflected light is deflected by facets 145 so as to be coupled-in to waveguide 120, is deflected at facets 140 so as to be coupled-in to waveguide 110, and some of it is reflected by PBS 105 onto a camera 125. In some embodiments, a polarization scrambler (not shown) is placed in front of PBS 105. Camera 125 is focused to infinity, analogously to projector 102 thereby an image of the retina is generated in the camera.

Figure 8:
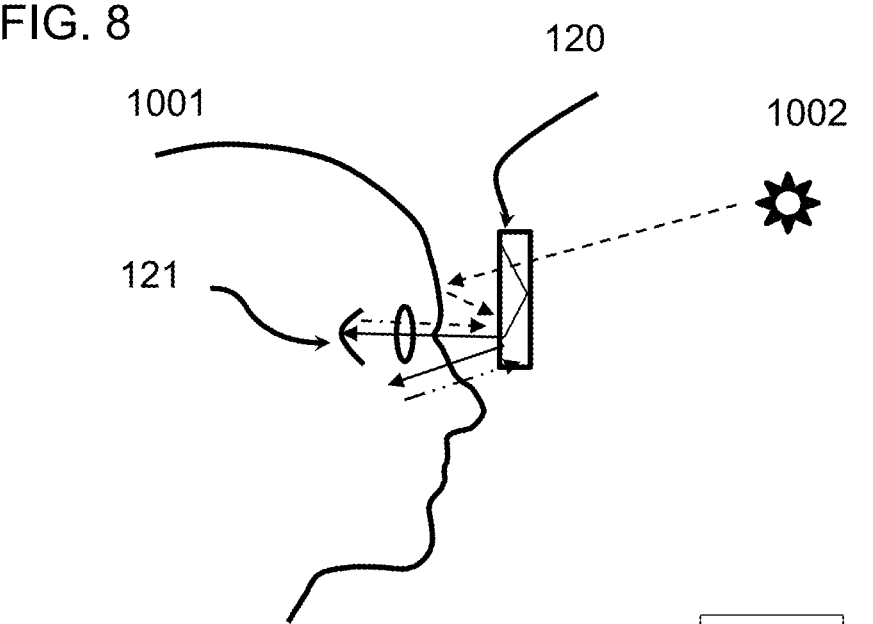
FIG. 8 is a schematic representation of an apparatus of the present invention illustrating the various sources of optical signal and optical background noise.

The various sources of illumination which may play a role in the imaging process are schematically depicted in FIG. 8. The waveguide 120 is deployed in facing relation to the eye of an observer 1001, meaning that the observer's view of a scene passes through the waveguide. External light sources 1002 (dashed arrows) illuminate the waveguide and the observer. This external light is continuous and enters the optical system as background radiation. The light generated by the optical system (solid arrows) illuminates the retina 121 and the face of the observer. The reflections from the retina (dash-dot arrow) are the signal of interest while the reflections from non-retina tissue surfaces (dash-dot-dot arrow) are additional background radiation that are intensity-correlated with the illumination pattern of the system. Any internal scattering within the system has the same characteristics as the light scattered from observer's face.

All background illumination causes noise that degrades the quality of the retina image. In order to reduce the effects of external illumination sources 1002, according as aspect of the invention, a short pulse of light (preferably below 1 ms) is used, and the camera is synchronized to integrate light only during this short illumination duration. In this manner, continuous background illumination is greatly suppressed. Additionally, or alternatively, a passband spectral filter 127 (shown in FIG. 7B) may be deployed to obstruct light of wavelengths outside a given range of wavelengths within which the eye-tracking illumination is generated from reaching the optical sensor.

There follows an estimation of the background light caused by illumination reflections (the dot-dot-dash arrow in FIG. 8) in order to derive the amount of light required for eye detection. This estimation, and all other discussion of operating principles and calculated values presented herein, are given only for the purpose of providing a fuller understanding of the invention, but do not in any way limit the invention other than as explicitly recited in the claims. Specifically, in the event that any specific calculation or value presented here might later be found to be imprecise or erroneous, such fact would not negate the utility of the invention as described herein.

Normal background surface reflects the light to pi steradian (assuming that the surface is a low sheen surface which generates a reflected light distribution approximating to Lambertian reflection), while the pupil generates a directional reflection corresponding to the "red eye" effect often observed in flash photography, reflecting light received from the optical system back into the optical system. Consequently, the intensity of the light received from the retina is stronger than equivalent background surface. Additionally, the image from the retina is focused at the image plane of camera 125 while illumination from nearby "background" surfaces is not. This improves ability to distinguish the image of the retina from image content derived from the background.

Figure 9A:
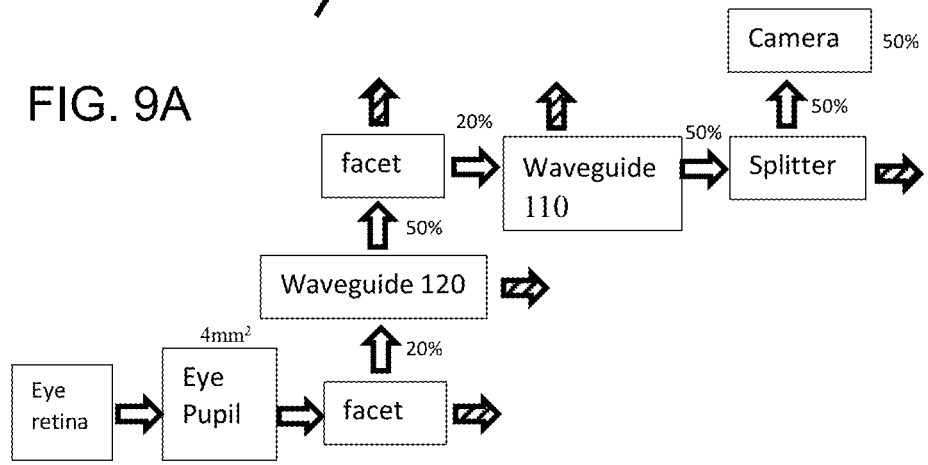
FIGS. 9A and 9B are schematic flow diagrams illustrating the sequential intensity losses of the optical signal and the optical background noise, respectively, along the respective optical paths to a camera.
Figure 9B:
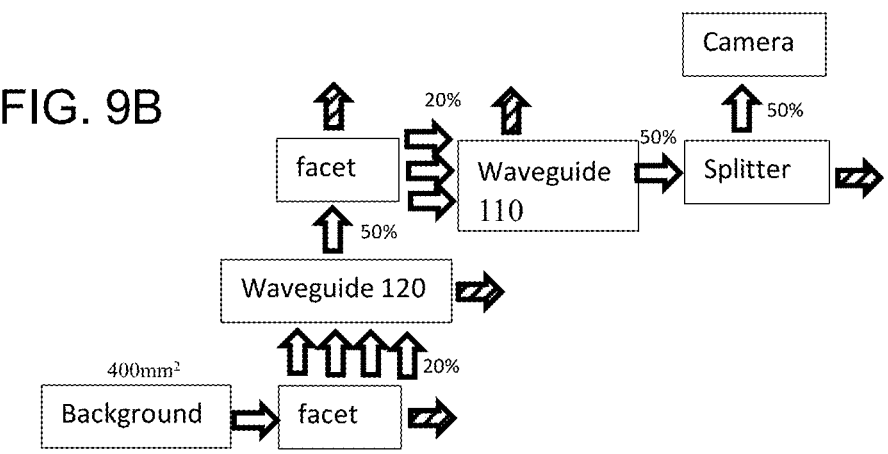

FIGS. 9A and 9B depict the light energy loss of the return path from the eye to tracking camera 125 and for background illumination.

The pupil of the human eye in bright light is of the order of 4 mm$^2$, while the eye-box (the area within which the image is visible, corresponding to the area illuminated by the system and which generates background reflection) can be roughly 400 mm$^2$. Assuming that the amount of illumination and the scattering coefficient are roughly the same for both the signal and the background, the ratio of reflected background to the signal is R=2×100=200 (assuming that the external tissues within the eye-box may be roughly twice as reflective as the retinal tissue. The following equations show the required signal for predefined SNR assuming a shot-noise limited camera:

$$\text{Background} = \text{Signal} \times R$$

$$\text{Noise} = \sqrt{\text{Background}}$$

$$SNR = \frac{\text{Signal}}{\text{Noise}} = \frac{\sqrt{\text{Signal}}}{\sqrt{R}}$$

$$\text{Signal} = SNR^2 \times R$$

Therefore, for required SNR of 5, the required number of photons is

Signal=SNR$^2$×R=5$^2$×200=5000[photoelectrons/frame/feature]

where 'feature' can be a pixel or a pattern to be detected with the defined SNR.

In this calculation, it was assumed that no other background light enters the system. Therefore, according to this invention, waveguide edges (126 in FIG. 1) are preferably absorbing or within an absorbing enclosure. This ensures that background radiation loses energy as it propagates in the optical waveguide, in the same manner as the signal from the retina, and doesn't gain energy.

The energy transmittance along the optical system can approximated in one non-limiting example as follows:
- 20% coupled into waveguide 120 via one of facets 145,
- 50% transmission along waveguide 120 (through additional facets 145 etc.),
- 20% coupled into upper waveguide 110 (if present) via facets 140,
- 50% transmission along waveguide 110,
- 50% coupling into camera 125, such as via PBS 105,
- 50% optical transmission and quantum efficiency of camera 125.

All of the above results in an estimated 2.5e-3 transmittance. Other degradation factors such as the modulation transfer function (MTF) and internal scattering can be approximated as another factor of 10 to result as 2.5e-4 transmittance.

In an embodiment where waveguide 110 is not present, the transmittance is higher and, using the above estimations, will be in the order of 2.5e-3.

It follows that the eye should receive approximately 5000/2.5e-4=2e7 photons during the integration time of every frame. For photon energy of 3 e-19J (red) this is approximately 6e-12 [J/integration time/feature], or 6 [nW/feature] for a 1 ms integration time. This is practical intensity of illumination.

Background scattering is substantially reduced if only selected sections of the retina (and corresponding selected directions of rays reaching other regions of the eye-box) is illuminated as proposed in certain implementations of the invention discussed further below.

Care should be taken to ensure that the eye tracking illumination does not disrupt the observer's perception of a projected virtual image. A number of approaches may be used to avoid disruption of the displayed image, including one or more of the following:

Employing low intensity;

Combining the tracking illumination as part of the projected image;

Selective tracking illumination directed towards insensitive or irrelevant regions of the retina;

Choice of tracking illumination wavelength so as to work with wavelengths to which the eye is insensitive, but that the optics can transmit and the camera can detect.

Each of these will now be addressed separately.

Low intensity: According to this approach, it is preferred to use a camera that is highly sensitive and has low internal noise, thereby allowing effective imaging of the retina with good SNR even at low illumination intensities. This allows use of sufficiently low intensity tracking illumination that the observer will not notice the illumination. The intensity should still satisfy the SNR calculation outlined above.

Figure 10:
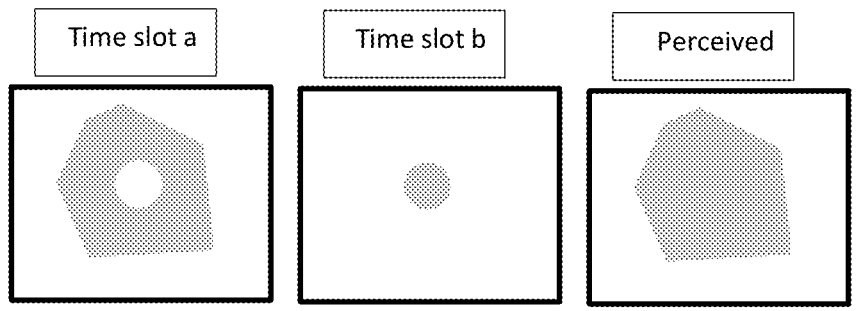
FIG. 10 is a schematic representation illustrating the subdivision of image data spatially between a regular image channel and a tracking illumination channel.

Combining illumination: The eye tracking illumination may be incorporated as part of the projected image. The illumination can be during image projection or in separate time slot as depicted in FIG. 10. In this example, during a time slot 'a', the image projector projects an image with missing or suppressed region. This illumination can be a relatively long duration, for example in the order of 10 ms. During a time slot 'b', a complimentary image is illuminated as a short pulse, for example, about 1 ms duration, at a higher intensity than the longer pulse, and serves as the eye tracking illumination, in addition to completing the image projection. The right-hand image represents what is perceived by the brain which integrates the two illumination periods. The complimentary image can be in any one of the color separations, or a combination of display colors, and at any selected location or locations within the image. One example of preferred "pattern control" for this illumination is described below.

It should be noted that the representation of FIG. 10 relates to the image plane of the projector and the image formed on the retina. Within the waveguides and in the light exiting the waveguides within the eye-box, each pixel corresponds to a broad collimated beam with a particular angular direction. The use of a selective pattern as illustrated schematically in FIG. 10, time slot 'b', corresponds to illumination in a small number of selected angular directions within the field of view.

Figure 11:
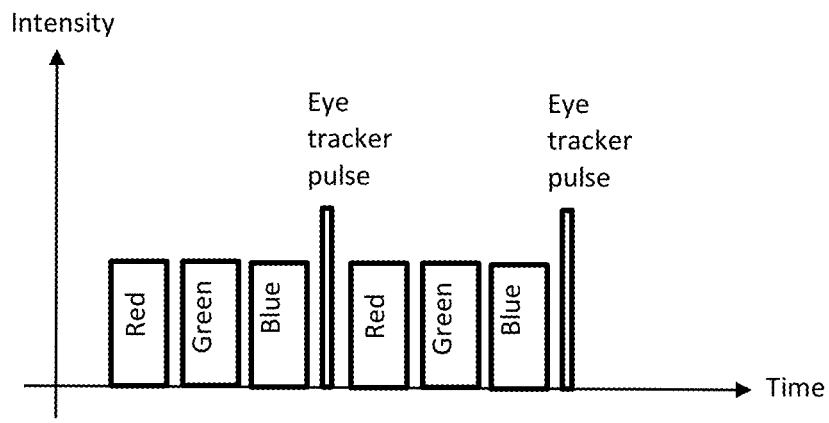
FIG. 11 is a schematic representation illustrating the subdivision of image data temporally between a regular image channel and a tracking illumination channel.

Illumination pattern control: Particularly where the image generator 102 (in FIG. 6B or 7B) is used to generate the eye tracking illumination, it is possible to conveniently control the illumination pattern on the retina, thereby illuminating only a region of interest and reducing disruption to the perceived image. In order to do so, the time sequence of illumination should be combined with the image projection timing. An example of time management of such an implementation is depicted in FIG. 11. In certain implementations, a set of light sources are activated in sequence in order to generate all colors. When each light source is illuminating, a modulation matrix (LCOS, LCD or MEMS) generates the required image of this color. The combination of the individual sources in fast sequence together with the modulation of every pixel generate the required color of every pixel in the image as it is perceived by the cells on the retina of the observer. According to certain implementations of the present invention, an additional time slot is introduced into the sequence of illumination (labeled 'eye tracker pulse'). In this time slot, one of the sources (colors), or a combination of sources, and/or a dedicated eye-tracking wavelength source (discussed below), is activated as a short pulse and its illumination pattern is determined by the modulator to illuminate only required sections of the retina. The eye tracking camera 125 is actuated by processing system 108 to integrate photoelectrons only during this pulse time.

This selected illumination pattern reduces significantly the background noise, since the selected regions of the retina to be tracked are fully illuminated, but the total amount of radiation delivered diffusely to the eye-box area is reduced according to the proportion of pixels that are "active" in the image.

Figure 12:
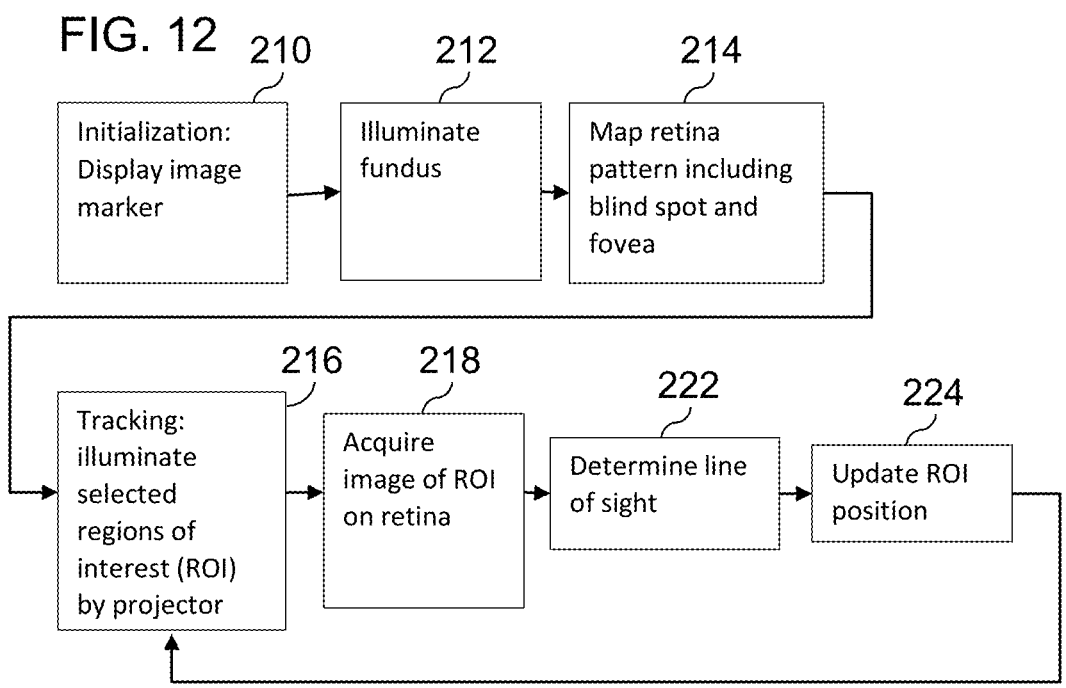
FIG. 12 is a flow chart illustrating a process for providing selective illumination for eye tracking according to an aspect of the present invention.
Figure 13:
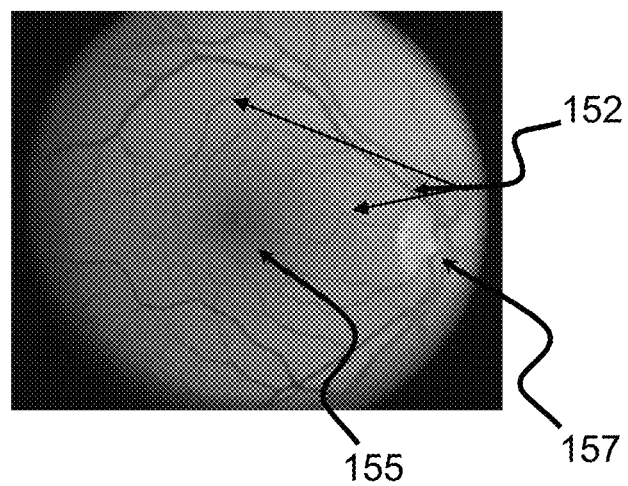
FIG. 13 is an image of the fundus of a human eye indicating various candidate features for use in tracking algorithms.

The illumination pattern can be concentrated only at specific points of interest on the retina, for example at the optic disc ("blind spot" 157 in FIG. 13), which has a characteristic blood vessels pattern but minimal sensitivity to light. The actual line of sight of the observer is calculated as an angular offset from this point. A non-limiting but particularly preferred process for deriving and tracking the actual line of sight is depicted in FIG. 12. The first three steps are an initial setup process for mapping the retina pattern and determining tracking features, while the subsequent steps represent a continuous tracking process. Specifically, at step 210, an image marker is displayed to the observer for the observer to look at during initialization. While the observer looks towards the marker, the fundus (visible portion of the retina) is illuminated fully by short pulses (step 212) and a full image of the fundus obtained. This image is then processed by processing system 108 to identify trackable features, typically including the optic disc and the fovea (step 214). Ongoing tracking of the eye direction then proceeds as follows. Selected regions of interest (ROI) are selectively illuminated, typically by sequences of illumination as described above with reference to FIGS. 10 and 11 (step 216), and an image is sampled during the corresponding illumination pulse (step 218). The resulting image is processed to determine the current line of sight (step 222), and this derived line of sight is used to update the position of the regions of interest (step 224) for the subsequent cycle of illumination cycle, and the tracking process returns to step 216. Assuming that the frequency of the tracking measurements is high compared to the speed of motion of the eye, this update process is typically effective to maintain continuous tracking, optionally combined with tracking information from the other eye. As the direction of the line of sight changes, so does the illumination area. Updating of the regions of interest may be performed according to the "current" gaze direction as determined from the last sampled image or, in certain cases, may use predictive extrapolation based on eye motion between the previous two or more measurements. In the event that tracking fails, the size of the illuminated region can be temporarily increased until the trackable features are recovered.

According to certain particularly preferred implementations of the present invention, the eye tracking arrangement is duplicated for tracking both eyes of a subject simultaneously. By combining data from two eye trackers, is may be possible to achieve enhanced stability and continuity of tracking. For example, while the eyes are moving, the optic disc 157 may be visible to the tracker in one eye and not the other. If a tracking algorithm is used which employs tracking of the blind spot, simultaneous tracking for both eyes allows the tracking to be maintained continuously through periods in which only one eye-tracker can track the blind spot.

Figure 14:
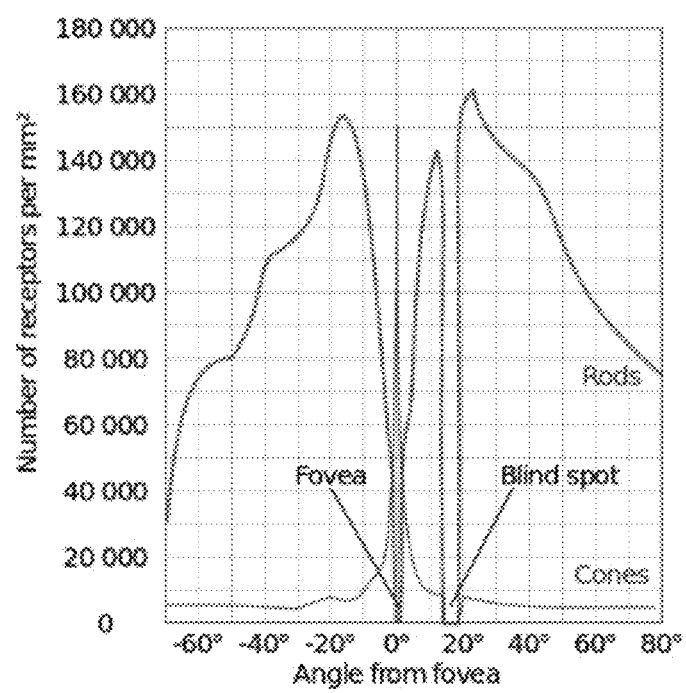
FIG. 14 is a graph illustrating the variation of the numbers of rod and cone photo-receptors in the human eye as a function of angle from the fovea in a plane passing through the optic disc.
Figure 15:
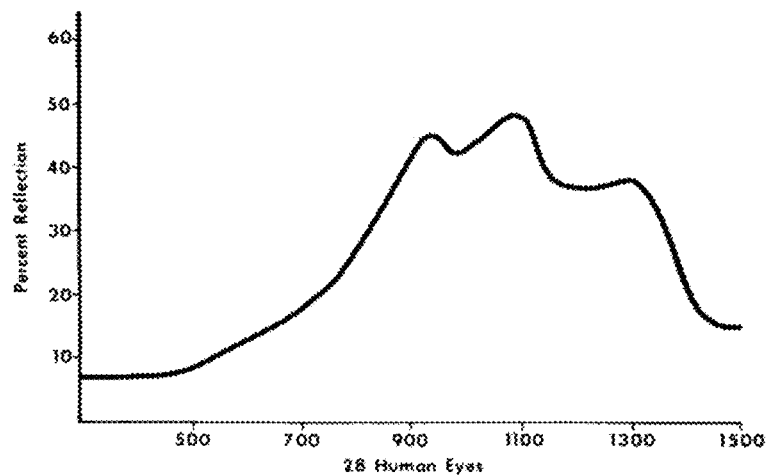
FIG. 15 is a graph illustrating the variation of reflectivity of the human retina as a function of wavelength over the visible light and infrared regions of the spectrum.
Figure 16:
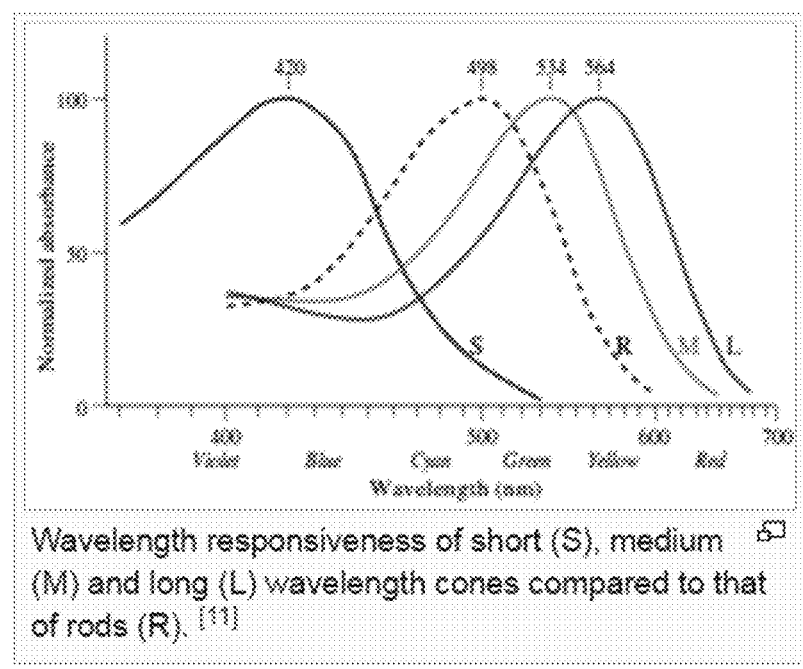
FIG. 16 is a graph illustrating the wavelength responsiveness of the different types of cone photo-receptors and rod photo-receptors in the human eye.

Wavelength selection: Referring to FIGS. 14-16, spectral sensitivity can also be used for minimizing stimulation of the eye during eye-tracking illumination. As illustrated in FIG. 14, rod cells are primarily responsible for the peripheral vision and are absent from the fovea. Rod cells are relatively insensitive to red (above 620 nanometers), as shown by graph 'R' in FIG. 16. The reduced number of cones that are present in the peripheral region are much less sensitive to low light levels than rods. Therefore, according to certain implementations of the invention, it is preferable to illuminate the peripheral retina (i.e., other than the fovea) with red light for the eye tracking.

It is apparent from the graph in FIG. 15 that reflection from the retina is substantially higher in the infrared than at visible wavelengths. At 700 nm, the reflection is almost double that of visible red. It may therefore be advantageous to employ a wavelength which is at the fringe of the visible-infrared (between 650-750 nm, and most preferably 680-720 nm), since scattering within the optical system is reduced and the optical coatings of the waveguide have almost the same reflectivity as in visible light, while the eye is insensitive to these wavelengths.

Longer wavelengths (900 nm for example) has up to 6 times more reflectivity than in the visible range, and can be used according to the present invention. This however requires optimization of the optical coatings in order to ensure that the required reflectivity of the various surfaces is suited also to the eye tracker wavelength.

Where infrared illumination is used for the eye tracker, there are various options for providing the infrared illumination. Where a wavelength of near infrared close to visible wavelengths is used, infrared illumination may be combined as a fourth "color" in the conventional visible image projection arrangement, for example, using an LCOS modulator. If patterned illumination is desired for longer wavelengths of infrared, a digital light processing (DPL) device is typically preferred. For non-patterned illumination, a dedicated illumination source is typically provided independent of the image projector. FIGS. 17A-20 illustrate certain implementation options for apparatus according to the present invention incorporating IR illumination into the optical system.

Figure 17A:
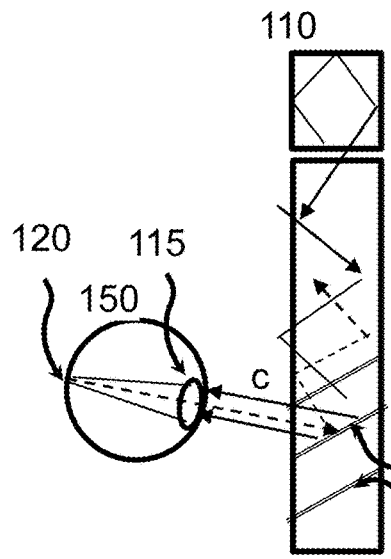
FIGS. 17A and 17B are schematic side and front views, respectively, of the optical architecture of the apparatus of FIG. 5 according to a further preferred implementation.
Figure 17B:
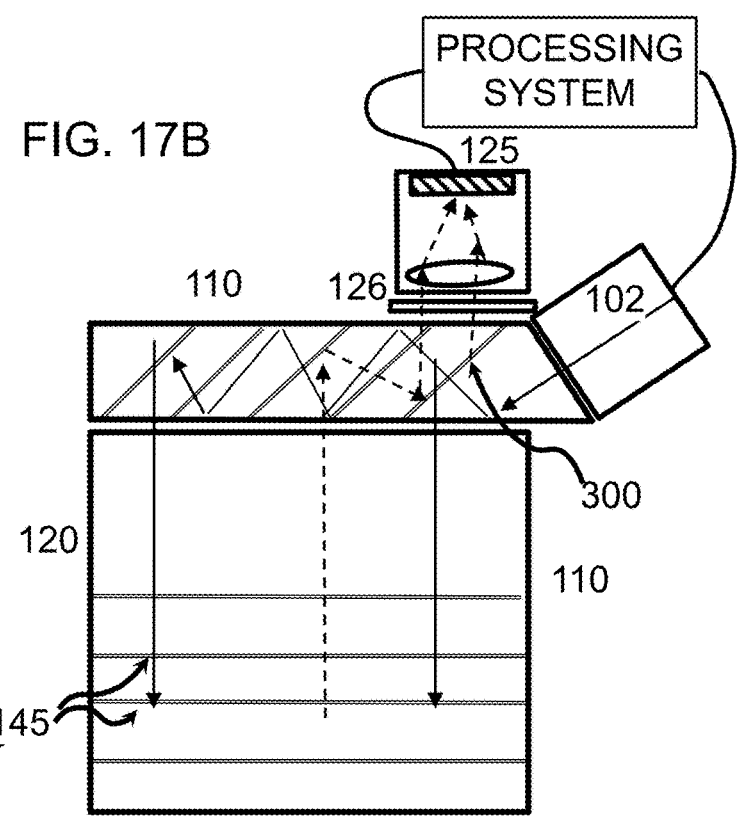

Referring first to FIGS. 17A and 17B, this relates to an implementation in which near infrared illumination is delivered by integration of a near-infrared source into the visible image projector arrangement as an extra "color". Details of the projector are not shown, but will be self-explanatory to one ordinarily skilled in the art. The eye detection camera is in this case placed adjacent to the upper waveguide 110 so that PBS 105 of FIG. 6B is not needed. This configuration is based on the fact that the internal facets 140 in LOE 110 couple upward the light that propagates from left to right. In this configuration, it is possible to introduce a polarizer 126, in order to minimize transmission of scattering.

Figure 18A:
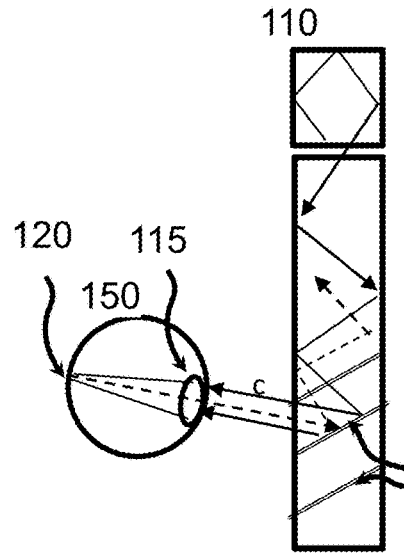
FIGS. 18A and 18B are schematic side and front views, respectively, of the optical architecture of the apparatus of FIG. 5 according to a still further preferred implementation.
Figure 18B:
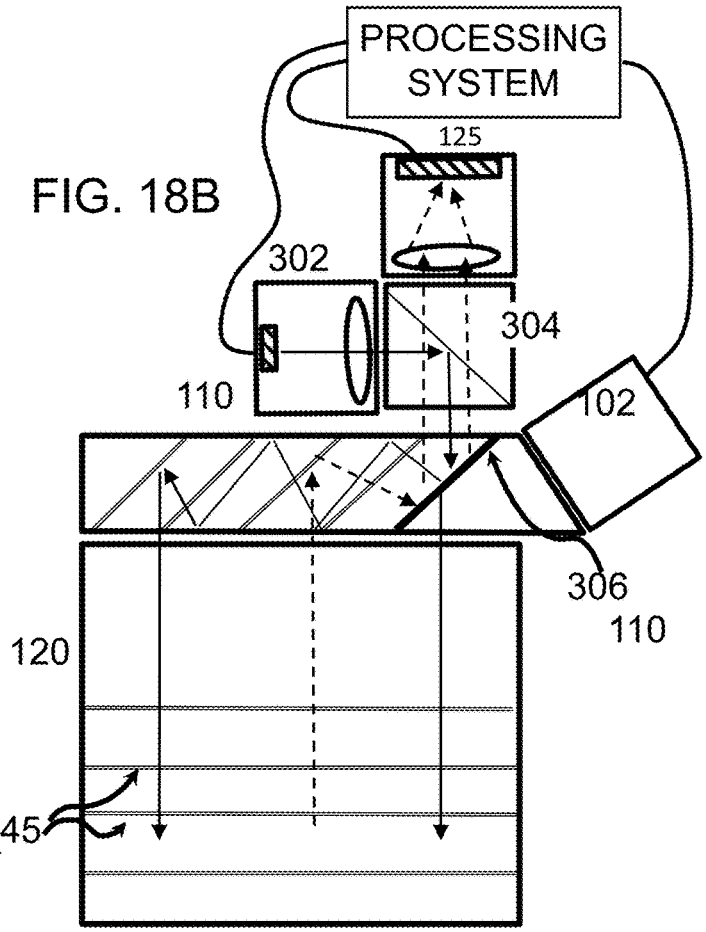

FIGS. 18A and 18B illustrate a further configuration in which a light source 302 having a wavelength different from the output of image projector 102 (can be IR or VIS, hereafter referred to as IR) transmits the light through a beam splitter 304 (which may be for example a 50/50 beam splitter or a PBS) into waveguide 110. The first facet 306 is designed to transmit all or most of visible light from the image projector 102 but is reflective for the IR light for the eye tracker. The IR illuminating light propagates to the eye and back as described in FIGS. 6A and 6B. It is then reflected by 306 to the beam splitter 304 and transferred to imaging camera 125.

Figure 18C:
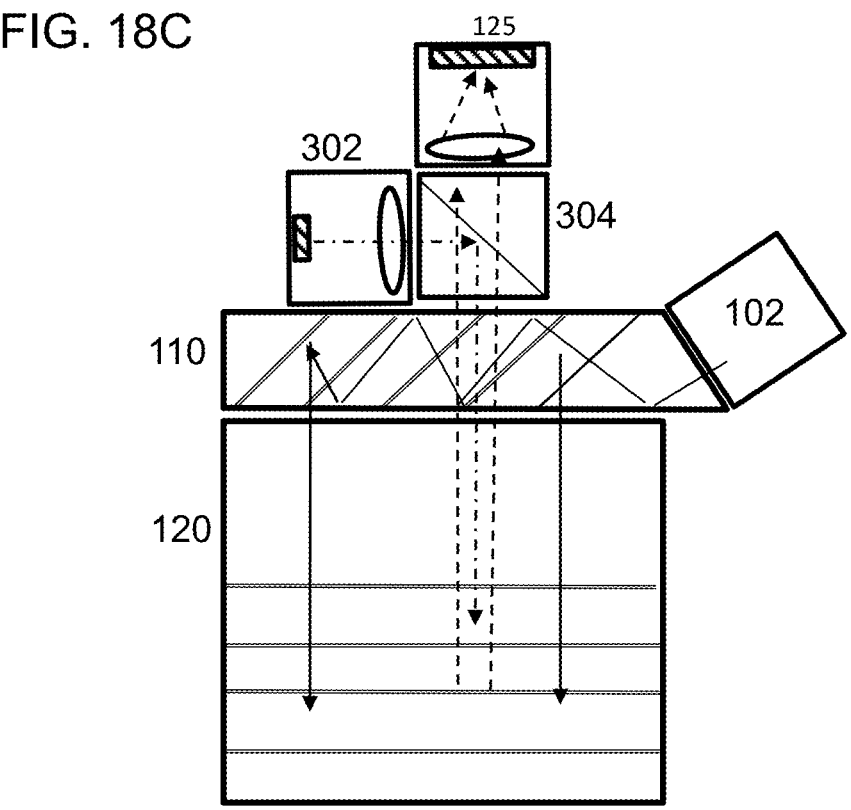
FIG. 18C is a view similar to FIG. 18B illustrating a further variant implementation.

In FIG. 18C, the returned light (dashed arrows) is reflected directly into the imaging camera 125 by transmission through waveguide 110 without being reflected and guided by this waveguide. This may require a wider receiving optics (similar to the arrangements used in a single waveguide projection arrangement such as in FIGS. 7A and 7B) and/or may have smaller receiving eye-box than the projector. The smaller eye-box is typically acceptable since (unlike the image projector) reflection from the eye can be at off-axis angles, as discussed further below with reference to FIGS. 21A-21C. The illumination can be from the image projector or from a dedicated illuminator 302 as shown.

Figure 19:
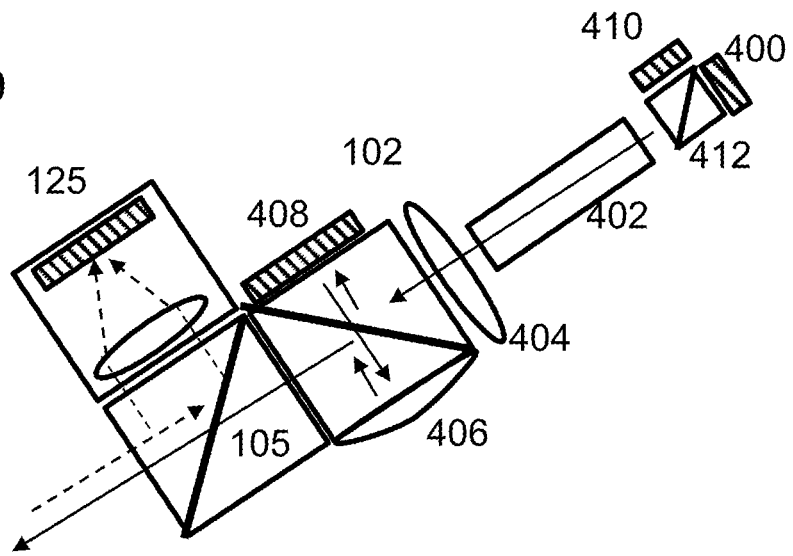
FIG. 19 is a further schematic front view of the optical architecture of a combined visible image projector and infrared illumination and imaging system, for use in the apparatus of FIG. 5.

FIG. 19 shows schematically further details of a possible implementation of projection system 102 for introducing IR illumination along with the visible (VIS) image projection. Light from VIS LED 400 passes through light pipe 402 (optional feature for enhancing uniformity), through illumination optics 404, through beam splitter 406 and onto LCOS 408. If the LCOS has embedded color filter per pixel then there is no light pipe in the system and the illumination is by white VIS LED. The IR LED 410 for eye-tracking is introduced through dichroic splitter 412. The IR LED is illuminating in sequence or simultaneously with the VIS LED.

Figure 20:
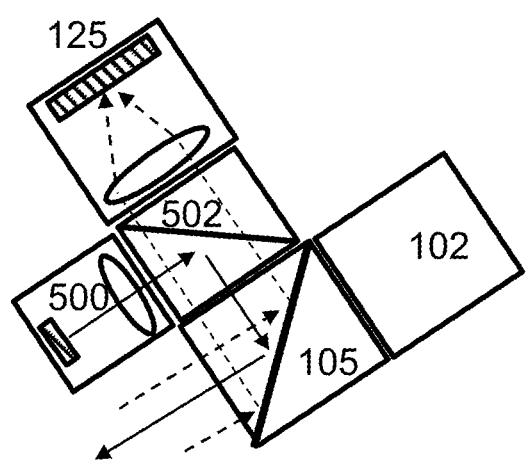
FIG. 20 is a further schematic front view of the optical architecture of a combined visible image projector and infrared illumination and imaging system according to a further variant, for use in the apparatus of FIG. 5.

FIG. 20 illustrates a further option, corresponding to the configuration shown in FIG. 6B. In this case, 102 is the image projection optics (not shown in detail) and 105 is a beam splitter. In this case however, 105 is preferably a dichroic beam splitter that transmits the visible light from the projector but reflects the IR light to and from the eye-tracking system. Clearly, a dichroic beam splitter with the opposite properties can be used to construct an equivalent configuration with the IR tracking system in the transmitted direction.

The IR illumination for the eye-tracking system is generated by an IR LED 500, the light passes through a beam splitter 502 (which may be a 50/50 beam splitter or a PBS) onto dichroic splitter 105 and reflected onto the waveguide (adjacent to beam splitter 105 but not shown in this drawing). The reflected light (dashed arrows) follows the reverse path and passes through beam splitter 502 onto the IR camera 125.

Figure 21A:
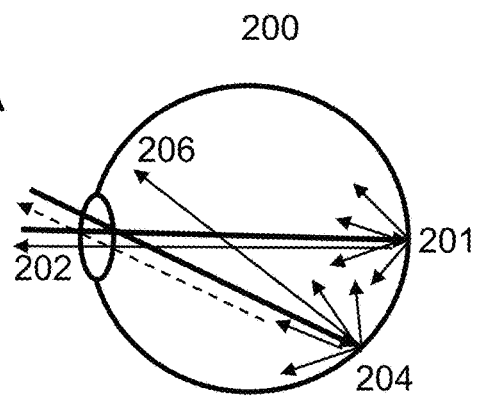
FIG. 21A is a schematic side view of a human eye illustrating the geometry of specular and diffuse reflections for different incident angles.
Figure 21B:
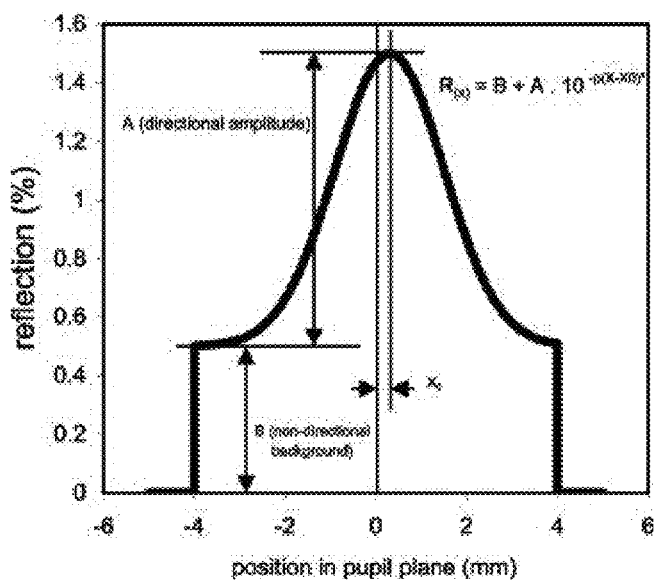
FIG. 21B is a graph based on theoretical calculations illustrating the variation in reflection of illumination from the retina as a function of angle (varied by changing pupil offset)
Figure 21C:
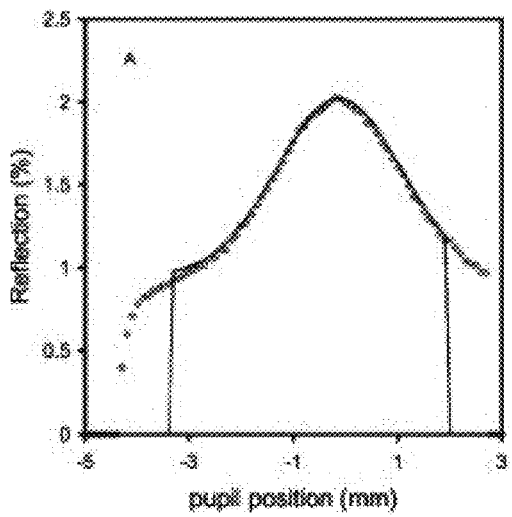
FIG. 21C is a graph similar to FIG. 21B based on experimental data.

Although described thus far in implementations in which detailed features of the retina are tracked, certain implementations of the present invention employ alternative tracking techniques. The reflection from the retina typically includes both a specular component and a diffuse, as illustrated in FIGS. 21B and 21C. A simplified model of the eye 200 in FIG. 21A shows an on-axis light ray impinging perpendicularly on the center of the retina 201. The strong specular reflection 202 is reflected through the entrance pupil therefore this reflection is strongly detected externally. However, when the light impinges on the retina at off axis angle 204, the specular reflection 206 does not exit the pupil and only the defused reflection exits the pupil (marked as a dashed arrow). This is a much weaker signal to be detected externally.

Figure 21D:
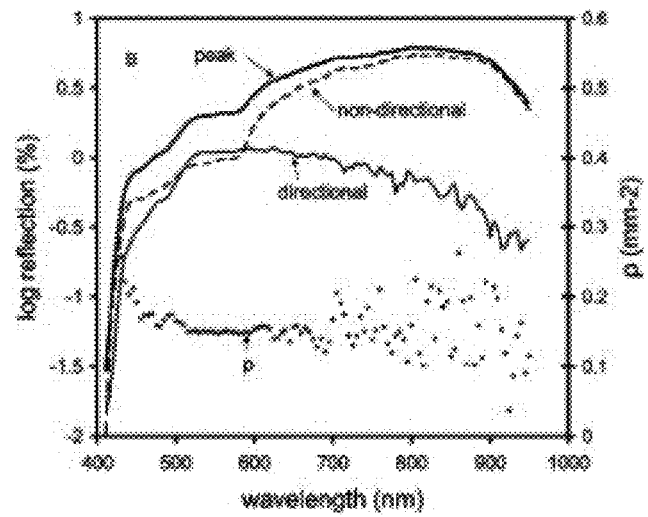
FIG. 21D is a graph illustrating variation of retinal reflectivity as a function of illumination wavelength.

The graph of FIG. 21B shows schematically the combined reflection intensity. The specular reflection component (characterized as variable amplitude A) is angularly dependent (here described as pupil position) while the diffuse reflection is roughly constant (characterized as amplitude B). The graphs of FIGS. 21C and 21D show experimental measurements and wavelength dependency for the components of the reflection. According to these experiments, the full-width at half maximum (FWHM) of the reflection is approximately a 2 mm pupil shift, corresponding to roughly ~10°. The actual resolution of the detection can be approximated as:

$$D\theta \approx FWHM/SNR$$

Since the SNR can be in the range of 10 to 100, The eye orientation resolution can be 1° to 0.1°. Signal processing for accurate orientation detection is known and an example is described in the paper "Sampling-balanced imaging system utilizing whitening matched filter" by Y. Danziger, Applied Optics Vol. 49, Issue 17, pp. 3330-3337 (2010).

It is therefore understood that the envelope of the intensity of the reflection from the eye back into the waveguide of the present invention will be angularly limited. This characteristic is used by certain implementations of the present invention to determine the orientation of the eye (independently from pattern detection).

Figure 22:
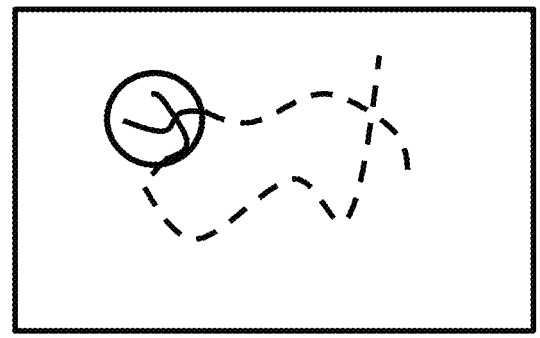
FIG. 22 is a schematic representation of a tracking image derived by an eye tracking subsystem of the apparatus of FIG. 5 in a case of angularly selective tracking illumination.

According to this aspect of the present invention, the entire field of view is preferably illuminated while only part is reflected by the eye. FIG. 22 depicts schematically the reflected field where the circle represents the strong specular reflection of the retina while the surrounding is weakly reflected. Therefore, the retina patters will be very visible within this circle but less apparent outside (depicted as dashed lines). According to this invention, the orientation of the eye will be observed as movement of the patterns and of the "envelope" of high reflection.

Unlike the previously discussed pattern detection, which will typically require an extensive sensor matrix, envelope detection of the sort described here requires much lower resolution, and may be performed using a four-quadrant or "quadrature" detector, or a low pixel count detector of less than $10^4$ pixels, and typically no more than 50×50 pixels, such as is common in an optical computer mouse. For this group of implementations, it may in some cases be advantageous to deploy the optical sensor 125 slightly displaced from the focal plane of focusing optics 106 in order to slightly defocus the image, thereby reducing or avoiding pixilation-related effects. The reduction in the number of sensor elements allows the use of high-speed graphics processing, which in turn contributes to the response speed of the tracking process.

Although the examples described thus far have combined the eye tracking illumination and imaging in a single waveguide, it should be noted that it may in some cases be advantageous to split these two functions between two separate waveguides. Specifically, in certain cases, there is a risk that internal scattering of the eye tracker illumination before it reaches the eye may give rise to sufficient back-scattered radiation to saturate the receiving camera. One approach to circumventing this problem is to minimize back scattering of illumination in the transmitting waveguide, such as by introducing smooth coatings or a glass layer on the face of the waveguide. An alternative approach is illustrated schematically in FIG. 23, where the transmitting and receiving functions are subdivided between two waveguides.

Figure 23:
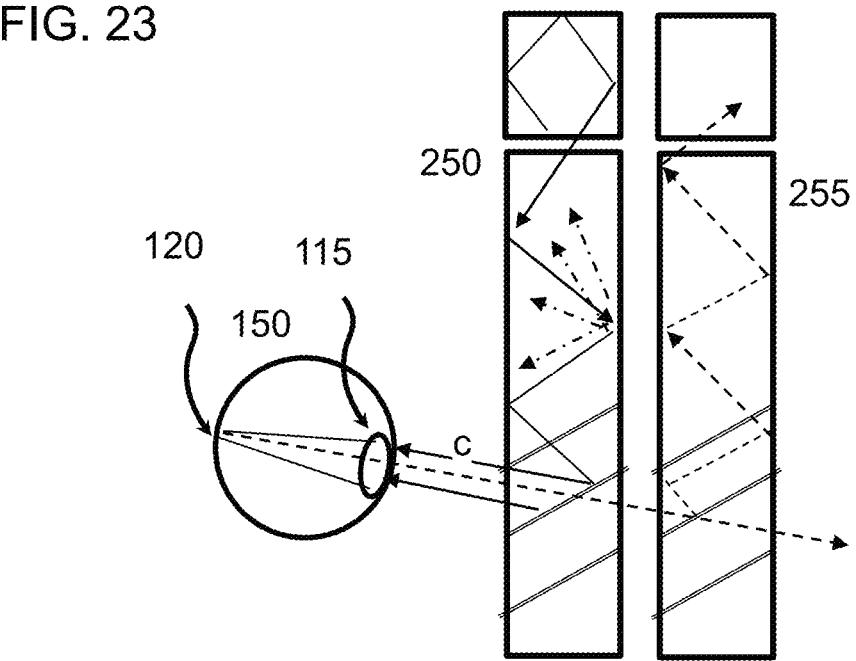
FIG. 23 is a side view of the optical architecture of the apparatus of FIG. 5 according to a further preferred implementation in which a dedicated light-guide optical element is provided for sampling retinal images.

Specifically, in the exemplary embodiment of FIG. 23, an augmented near-eye display 250 can be any type that delivers an image illuminates the eye. In this side-view illustration, it is shown as employing a combination of a 2D waveguide and a 1D waveguide, all based on partially-reflective facets, but all of the additional options mentioned above apply here also. In this figure, the dot-dash arrows represent one scattering point (of which can be many) that could saturate combined transmitter/receiver waveguide.

As before, the illumination can be with a visible illumination or by IR wavelength. In the implementation illustrated here, the reflected light from the eye is collected by a parallel waveguide 255 (shown in side view), distinct from the illumination light-guide element. In this case, both light-guide optical elements are as described above, formed from transparent material and having pair of parallel faces for guiding light by internal reflection, and are deployed in overlapping relation in facing relation to the eye of the observer.

The reflected light (depicted as dashed arrow) passes through the illumination waveguide 250 (that is anyway implemented to be mostly transparent in order to allow the observer to see the real world) and into the receiver waveguide 255. This waveguide is also mostly transparent, but also includes a coupling mechanism (facets or diffractive) for coupling part of the radiation into the waveguide. The reflected image propagates within this waveguide 255 and is collected by the receiver much the same way as previously described for the combined system.

Figure 5:
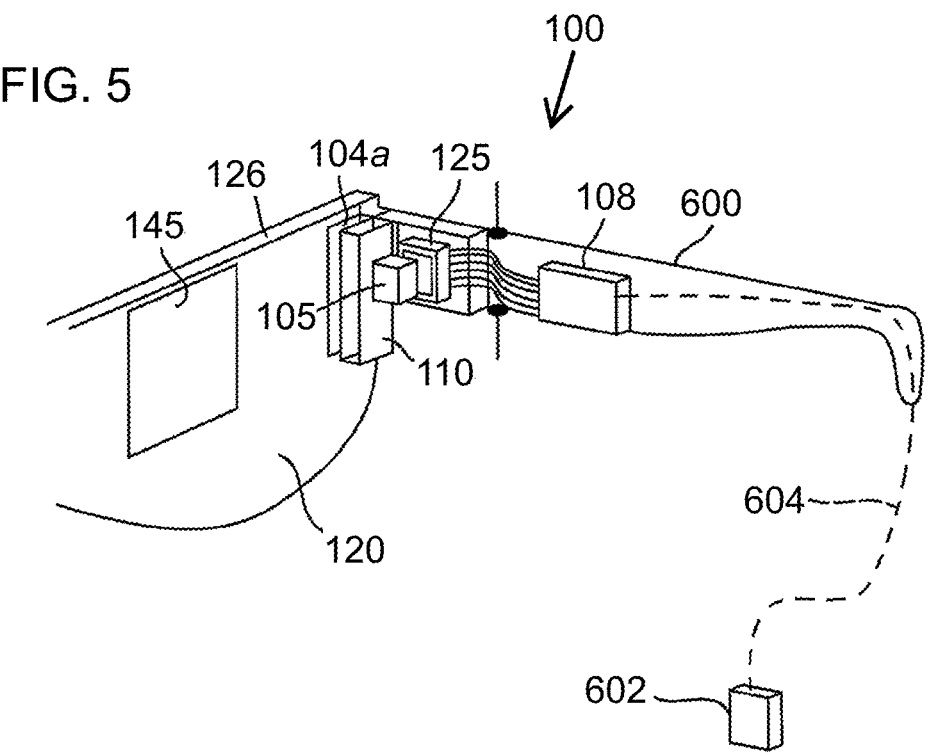
FIG. 5 is a partial schematic isometric view of an apparatus, constructed and operative according to an embodiment of the present invention, for tracking the gaze direction of a human eye combined with a near-eye display.

Turning briefly back to FIG. 5, according to the particular non-limiting implementation illustrated here, apparatus 100 is implemented in an eye-glasses form factor with side arms 600 for engaging the ears of the observer, although other form factors such as helmet-mounting etc. also clearly fall within the scope of the present invention. Processing system 108 may be implemented using any suitable type of processing hardware and/or software, as is known in the art, including but not limited to any combination of various dedicated graphics processors, display drivers, and general purpose processors operating under any suitable operating system and implementing suitable software or firmware modules. Processing system 108 typically also includes various volatile data storage and various communications components for allowing wired or wireless communication with LAN and/or WAN devices for bidirectional transfer of information and graphic content. The apparatus is powered from a suitable electrical power source, which may be any combination of batteries and/or an external power source provided, illustrated here schematically as power source 602 connected via a cable 604. Where battery power is used, the batteries may be integrated as part of the eye-glasses or helmet-mounted structure.

It will be noted that the eye tracking of the present invention fundamentally determines the angular orientation (i.e., gaze direction or "line of sight") of the eye, but is in most embodiments essentially insensitive to the spatial position of the eye relative to the apparatus, as long as the eye remains within the effective eye-box of the LOE coverage. As such, the apparatus exhibits profound advantages for eye-glasses type or other head-mounted devices and/or other wearable devices for which it is not always feasible to ensure precise and repeatable alignment of the system with the head, and/or where the system may move somewhat relative to the eyes during use.

As mentioned above, although illustrated here as a partial view of one side of the eye-glasses construction, the overall device may provide either monocular or binocular image projection and tracking, where binocular is particularly preferred for both. Where the apparatus is binocular, various processing and power-supply components may optionally be shared by the two tracking systems, and tracking information is preferably fused in order to provide enhanced stability and continuity of tracking, as discussed above.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

It will be appreciated that the above descriptions are intended only to serve as examples, and that many other embodiments are possible within the scope of the present invention as defined in the appended claims.

What is claimed is:

1. An apparatus for deriving a gaze direction of an eye of a user, the apparatus comprising:
    (a) a transparent light guide assembly for positioning in facing relation to the eye of the user and allowing the user to view a remote scene through the light guide assembly, the light guide assembly comprising:
        (i) a first light-guide optical element (LOE) having a first pair of parallel faces for guiding light by internal reflection between said first pair of parallel faces, said first LOE including a coupling-out configuration for deflecting light guided within said first LOE outwards towards the eye, and
        (ii) a second light-guide optical element (LOE) having a second pair of parallel faces for guiding light by internal reflection between said second pair of parallel faces, said second LOE including a coupling-in configuration for deflecting light received from the eye so as to propagate by internal reflection between said second pair of parallel faces within said second LOE;
    (b) a light source associated with said first LOE so as to introduce eye-tracking illumination into said first LOE to propagate by internal reflection between said first pair of parallel faces to said coupling-out configuration for coupling out towards the eye;
    (c) an optical sensing arrangement including converging optics deployed to converge a part of the eye-tracking illumination reflected from the eye, coupled in to said second LOE by the coupling-in configuration and propagating within said second LOE so as to converge onto an optical sensor and such that eye-tracking illumination back-scattered within said first LOE does not reach said optical sensor;
    (d) a processing system including at least one processor, said processing system being electrically associated with said optical sensor and configured so as to process signals from said optical sensor to derive a current gaze direction of the eye; and
    (e) a support configuration for supporting the apparatus relative to the head of the user so that said transparent light guide assembly is supported with said first LOE and said second LOE overlapping in facing relation to the eye of the user so that the user views the remote scene through both said first LOE and said second LOE.

2. The apparatus of claim 1, wherein said light source is implemented as an image projector coupled to said first LOE so as to introduce a collimated image into said first LOE such that said collimated image propagates via internal reflection within said first LOE and is coupled out of said first LOE towards the eye by said coupling-out configuration.

3. The apparatus of claim 1, wherein said light source generates light of a non-visible wavelength, the apparatus further comprising:
    (a) an image projector coupled to said first LOE so as to introduce a collimated image into said first LOE such that said collimated image propagates via internal reflection within said first LOE and is coupled out of said first LOE towards the eye by said coupling-out configuration; and
    (b) a passband spectral filter deployed to obstruct light of wavelengths other than said non-visible wavelength from reaching said optical sensor.

4. The apparatus of claim 1, wherein said coupling-in configuration comprises a partially-reflective surface deployed within said second LOE obliquely to said parallel faces.

5. The apparatus of claim 1, wherein said coupling-in configuration comprises a diffractive optical element associated with said second LOE.

6. The apparatus of claim 1, wherein said optical sensor comprises a four-quadrant sensor.

7. The apparatus of claim 1, wherein said optical sensor comprises an array of pixel sensing elements, and wherein said processing system processes outputs from no more than about $10^4$ pixel sensing elements.

8. An apparatus for deriving a gaze direction of an eye of a user, the apparatus comprising:
    (a) a transparent light guide assembly for positioning in facing relation to the eye of the user and allowing the user to view an image projected from said light guide assembly towards the eye of the user, the light guide assembly comprising:
        (i) a first light-guide optical element (LOE) having a first pair of parallel faces for guiding light by internal reflection between said first pair of parallel faces, said first LOE including a coupling-out configuration for deflecting light guided within said first LOE outwards towards the eye, and
        (ii) a second light-guide optical element (LOE) having a second pair of parallel faces for guiding light by internal reflection between said second pair of parallel faces, said second LOE including a coupling-in configuration for deflecting light received from the eye so as to propagate by internal reflection between said second pair of parallel faces within said second LOE;
    (b) a light source associated with said first LOE so as to introduce eye-tracking illumination into said first LOE to propagate by internal reflection between said first pair of parallel faces to said coupling-out configuration for coupling out towards the eye;
    (c) an optical sensing arrangement including converging optics deployed to converge a part of the eye-tracking illumination reflected from the eye, coupled in to said second LOE by the coupling-in configuration and propagating within said second LOE so as to converge onto an optical sensor and such that eye-tracking illumination back-scattered within said first LOE does not reach said optical sensor;
    (d) a processing system including at least one processor, said processing system being electrically associated with said optical sensor and configured so as to process signals from said optical sensor to derive a current gaze direction of the eye; and
    (e) a support configuration for supporting the apparatus relative to the head of the user so that said transparent light guide assembly is supported with said first LOE and said second LOE overlapping in facing relation to the eye of the user so that a line of sight of the user intersects both said first LOE and said second LOE.

* * * * *